US006251376B1

(12) United States Patent
Beck et al.

(10) Patent No.: US 6,251,376 B1
(45) Date of Patent: Jun. 26, 2001

(54) ANTIPERSPIRANT PRODUCT AND METHOD

(75) Inventors: Jon Beck; Jason S Burry; Helen F Coulson, all of Merseyside (GB)

(73) Assignee: Unilever Home & Personal Care USA, Chicago, IL (US)

( * ) Notice: Subject to any disclaimer, the term of this patent is extended or adjusted under 35 U.S.C. 154(b) by 0 days.

(21) Appl. No.: 09/395,950

(22) Filed: Sep. 14, 1999

(30) Foreign Application Priority Data

Sep. 14, 1998 (GB) .................................... 9819991

(51) Int. Cl.[7] ............... A61K 7/32; A61K 7/34; A61K 7/36; A61K 7/38; A61K 7/00
(52) U.S. Cl. ................ 424/65; 424/66; 424/67; 424/68; 424/400; 424/401
(58) Field of Search ................ 424/65, 66, 67, 424/68, 400, 401

(56) References Cited

U.S. PATENT DOCUMENTS 4,650,671   3/1987   Golman .................................. 424/66

OTHER PUBLICATIONS

International Search Report Applicatiion No. PCT/EP 99/06661 mailed Dec. 29, 1999.
Slegers, J. F. G. et al.: "Effect of Acetazolamide on the Chloride Shift and the Sodium Pump in Secretory Cells", Nature, vol. 220, No. 5163, 1968, pp. 181–182, XP002124877 (the whole document).
Chemical Abstracts, vol. 113, No. 16, (10/90) Abstract No. 138324, Lin, Zexong: "Antiperspirant Deodorants Containing Zinc Stearate and Others" —XP002124878 (Abstract) & CN 1,033,561 A (Peop. Rep. China) (7/89).

*Primary Examiner*—Shelley A. Dodson
(74) *Attorney, Agent, or Firm*—Matthew Boxer

(57) ABSTRACT

An antiperspirant product for the human skin, comprising an antiperspirant active for topical application, and an effective amount of a compound which inhibits the acidification mechanism in the eccrine gland to elevate the pH of sweat.

13 Claims, No Drawings

ANTIPERSPIRANT PRODUCT AND METHOD

This invention relates to antiperspirant compositions and to methods of improving the efficiency of antiperspirant compositions, and to cosmetic methods of inhibiting perspiration on the skin.

Cosmetic antiperspirant compositions are known, and typically comprise topically acceptable compositions containing a metal salt, such as an aluminium and/or zirconium salt, in combination with a cosmetically suitable vehicle. Such cosmetic antiperspirant products may be available in a variety of product forms, for example as sticks, roll-on lotions, aerosols and pump spray formulations to name a few.

Whilst such compositions provide a degree of perspiration inhibition, it has long been desirable to improve the efficacy of such topical compositions in order that a user may experience fewer wetness events. Further, if the efficacy of such products can be improved, it may be possible to devise products in which the concentration of the metal salt providing antiperspirant efficacy can generally be reduced, but whilst still providing products of equal or even higher efficacy. This could lead to such products being cheaper, easier to formulate (by virtue of the reduced amount of antiperspirant active used), or generally having improved sensory properties.

We have found that it may be possible to enhance the efficacy of known antiperspirant materials in topical compositions, such as contain actives, such as but not limited to aluminium and zirconium salts, by the addition to, or use with, the topical composition of a composition which raises the pH of sweat in the eccrine gland.

Thus, according to a first aspect, there is provided an antiperspirant product for application to the human skin, comprising an antiperspirant active for topical application and an effective amount of a compound which inhibits the acidification mechanism in the eccrine gland to elevate the pH of sweat.

Herein, the antiperspirant product can comprise the antiperspirant active and the compound which inhibits the acidification mechanism in the eccrine gland in a single composition for topical application or, alternatively, the product can comprise separate means for the administration of the aforementioned components. When the components are administered via separate means, they can be supplied in a pack, together with instructions for their administration. In using such a product, the components can be applied consecutively, or, for greater convenience, concurrently. In a preferred embodiment, both components are applied topically.

According to a further aspect of the invention, there is provided a cosmetic method of elevating the pH of sweat in the eccrine gland comprising topically applying thereto an effective amount of a compound which raises the pH of sweat in the gland.

According to a further aspect of the invention, there is provided a cosmetic method of preventing perspiration of the human body, comprising topically applying to the body a composition comprising an antiperspirant active, and also applying a compound which elevates the pH of sweat in the eccrine gland. For greater convenience, the two components involved in the method may both be topically-applied from a single composition.

Thus, according to a further aspect of the invention, there is provided an antiperspirant composition for topical application to the human skin, comprising an antiperspirant active, and an effective amount of a compound which elevates the pH of sweat in the eccrine gland.

In order to generate the elevation of sweat pH in an eccrine gland, we have found that this can be achieved by the inhibition of bicarbonate reabsorption in the eccrine gland, and as such the invention also comprises compositions and methods which comprise and utilize compounds which are topically applied and which inhibit the reabsorption of bicarbonate in the eccrine gland.

Bicarbonate reabsorption is a known transport mechanism, which operates in the eccrine gland. This is more fully described in "Biology of sweat glands and their disorders. I. Normal sweat gland functions" by Sato, Hang, Saga & Sato, Journal of American Academy of Dermatology, pp 537–563, Volume 20, No 14, April 1989. Without wishing to be bound by theory as to how the invention may work, it is suspected that by disrupting this reabsorption mechanism in the cell lumen, the pH of secreted sweat can be caused to raise by somewhere in the region of (but not limited to) 0.5–1 pH units. Such an elevation of pH in sweat prior to its arrival at the skin surface has been found to provide for the enhancement of efficacy of antiperspirant actives that gel better at pH values higher than those of unmodified sweat in the eccrine duct. Examples include (but are not limited to) aluminium, aluminium/zirconium, and zirconium salts, in topically applied compositions.

It is thus a preferred aspect of the methods and products of the invention that the compound which is capable of elevating the pH of sweat in the eccrine gland is a compound which inhibits the bicarbonate reabsorption mechanism.

In a further preferred aspect, the compound which inhibits bicarbonate reabsorption may be a carbonic anhydrase inhibitor. Suitable and preferred carbonic anhydrase inhibitors include acetazolamide, and especially ethyl tosylamide. Such compounds can be added to topical antiperspirant compositions to provide compositions which may have enhanced antiperspirant efficacy over other known compositions.

We have also found that the invention is particularly efficacious on areas of the human skin that excrete sweat having a naturally low pH; in particular, the skin of the lower back, the feet, the forehead, and the back of the neck.

The compound which is capable of elevating the pH of sweat in the eccrine gland when applied in conjunction with a topical antiperspirant composition will preferably elevate the pH of sweat by at least 0.05, more preferably by at least 0.1, even more preferably by at least 0.2 pH units. Conveniently the pH of sweat will not be elevated by more than 1.5 pH units, more preferably by not more than 1.0 pH units.

Antiperspirant active materials which may have their efficacy enhanced by the methods and products according to the invention are those that gel better at pH values higher than those of unmodified sweat in the eccrine duct, for example aluminium, aluminium/zirconium, and zirconium salts. Particular examples are: aluminium chlorohydrate, activated aluminium chlorohydrate, zirconium aluminium chlorohydrate, zirconium aluminium glycinate, and activated zirconium aluminium glycinate.

The invention is capable of being utilized with any suitable antiperspirant composition form, including (but not limited to) sticks, roll-on lotions, aerosols, and pump spray formulations. The antiperspirant active in such compositions is present at a level of 0.5 to 60%, particularly 5 to 30 or 40%, and especially from 10 to 30 or 35% by weight.

Acetazolamide (N-[5-sulfamoyl-1,3,4-thiadiazol-2-yl] acetamide) is a known compound, and is commercially available as Diamox powder from Wyeth Research UK Ltd. It has been clinically used previously as a diuretic, to ameliorate high altitude sickness, and to treat glaucoma and various forms of epilepsy. It has been found that the introduction of acetazolamide into eccrine glands leads to the elevation in the pH of sweat from that gland, and has also lead to the increase in efficacy of a conventional antiperspirant composition topically applied to those glands.

A further suitable compound suitable for use in conjunction with the topical antiperspirant compositions is Sibercizer C6 (N-ethyl-O and P-toluenesulfonamide), available from Merck. Other suitable compounds may include Dorzolamide (4H-Thieno[2,3-b]thiopyran-2-sulfonamide, 4-(ethylamino)-5,6-dihydro-6-methyl-,7,7-dioxide,(4S,6S)-(9Cl)) and Sezolamide (4H-Thieno[2,3-b]thiopyran-2-sulfonamide, 5,6-dihydro-4-[(2-methylpropyl)amino]-,7,7-dioxide, (S)-), together with cosmetically acceptable and effective salts and analogues of all of the above mentioned specific compounds. A preferred group of carbonic anhydrase inhibitors are the carbonic anhydrase inhibiting sulphonamides.

Thus, according to a further aspect of the invention, there is provided a cosmetic method of preventing perspiration in the eccrine gland, comprising topically applying thereto a compound which is capable of elevating pH of sweat in the eccrine gland, in conjunction with the application of an antiperspirant active. Preferably the compound which is capable of elevating pH of sweat in the eccrine gland is acetazolamide.

Suitable compounds for raising the pH of sweat are typically effective at levels of 0.01% or less by weight of the composition comprising the antiperspirant active, though any effective amount may be used. The upper limit of usage of the compound for raising the pH of sweat is likely to be dictated by factors such as cost, formulation considerations, and attainment of a plateau of the efficacy of the composition. Typical effective amounts are 0.005–0.1% by weight of the composition comprising the antiperspirant active, preferably 0.01–0.05% by weight of the composition comprising the antiperspirant active, administered together with, or independent of, the aforementioned composition.

The remaining components of the composition comprising the antiperspirant active will be those typically associated with the various forms of topical antiperspirant composition, including (but not limited to);

cosmetic vehicles, such as water, short chain monohydric and polyhydric alcohols, and silicones. Silicones may be of the volatile or non volatile variety;

emollients;

structuring and/or thickening agents, such as silicas, polymers, clays, long chain fatty alcohols such as stearic alcohol, and long chain fatty acids such as stearic acid;

perfumes;

masking oils, such as polydecene, or polyethylene glycol 14 butyl ether;

talc;

hydrocarbon or silicone waxes;

propellants

These components may typically form the balance of the composition comprising the antiperspirant active, and thus may for example comprise 65–98% by weight of the composition. Their exact nature will also depend on the product form, which can typically be an aerosol, pump spray, stick, soft solid, gel, roll on lotion, or cream. The antiperspirant active itself can typically be in the form of a solution, suspension, emulsion or microemulsion.

The invention will now be further described by way of illustration only, with reference to the following examples.

EXAMPLE 1

This example demonstrates in vivo the elevation of sweat pH caused by administration of acetazolamide.

The example utilised the technique of iontophoresis, which is further described in R R Burnett, "Ionotophoresis in Transdermal Drug Delivery", Eds J Hadgraft & R H Guy, published by Marcel Dekter Inc. 1989. In this method, accurate doses of compounds are delivered by transcutaneous iontophoresis to the skin in such a manner that normal passage of the material (especially ions) into the skin is facilitated. This quantitative administration of acetazolamide facilitated the measurement of the effect on sweat pH, and subsequently the efficacy of topically applied antiperspirant actives.

In the application method, a solution of acetazolamide was prepared in HPLC grade water and titrated to pH7 with sodium hydroxide solution (32% aqueous, ex J. T. Baker). The solution is then contained in a reservoir that is attached to the skin surface with double side adhesive tape. A platinum electrode in the chamber is connected to the appropriate terminal of a voltage source, and a reference electrode (for example an ECG electrode) is stuck on the skin some distance from the chamber to complete the circuit.

A suitable iontophoresis chamber is an Iomed Iontophoresis Drug Delivery System "Phoresar II" model PM700, ex Moor Instruments Ltd., Axminster, Devon. Test solutions may be administered through an acrylic chamber, also ex Moor Instruments, containing a platinum electrode; disposable Ag/AgCl ECG electrodes were used for reference to complete the circuit (ex Henley's Medical supplies, Hartford).

The quantity of substance delivered under these conditions depends on the charge of the ion, its molecular weight, the magnitude of the electric current and the duration of current flow, and is independent of the concentration of the substance in the aqueous solution.

To demonstrate the effect of the acetazolamide on sweat pH, a panel of 10 male volunteers had an area of skin prepared with a sterile wipe, and the iontophoretic chamber was secured on the skin, connected to the power supply and charged with acetazolamide solution. Application sites were usually on the back or forearm; control sites consisted of areas free of treatment, to provide a background reading, and an area was exposed to acetazolamide with no iontophoresis for 3 minutes, to measure the effect of surface contact. Three test sites were then exposed to the acetazolamide solution for 1, 2 and 3 minute iontophoresis periods, at currents of up to 500 microamps.

After treatment, excess solution is wiped from the skin, and the skin is wiped with distilled water.

Measurements of pH are made relative to a control, and compared to changes in pH observed in a similar protocol for application of a phosphate buffer, thereby providing a biologically inert control.

Application of acetazolamide is carried out at ambient temperatures. Measurements of sweat pH are subsequently made at 40° C. and 40% relative humidity after a suitable period of equilibration.

After the warm up period, the test sites are wiped clean with a tissue, and the pH of sweat from the test area is measured by placing a flat head pH electrode on the surface of the skin.

Results

Even with zero current applied to the ionotophoresis equipment, an elevation in sweat pH of 0.15 units relative to the phosphate buffer was observed (P<0.05). When a current was applied over periods of 1, 2 and 3 minutes, average pH increases of 0.40 pH units relative to the buffer solution were observed (P<0.0001).

EXAMPLE 2

This example measures the effect of elevating the pH of sweat on the efficacy of topical antiperspirant compositions.

In this example, the skin is prepared for iontophoresis as above, and test sites are isolated. Of the test sites, two are used for background readings and receive no treatment, whilst four other sites were used to test two antiperspirant compositions, each being tested on a site which had received acetazolamide iontophoresis pretreatment, and a site which had received no pretreatment.

Immediately following acetazolamide iontophoresis (or control) pretreatment, two antiperspirant compositions (A, a zirconium aluminium based composition, and B, an aluminium chlorohydrate based composition) were applied to the test sites from a roll-on lotion applicator.

The treated areas were then covered with a protective layer of gauze until the panellists were required to sit in a hot room at 40° C./40% relative humidity six to eight hours later.

| Composition | A | B |
|---|---|---|
| Component | % | % |
| Ethanol | 54.45 | 54.45 |
| Klucel M (1) | 0.8 | 0.8 |
| Rezal 67 (2) | 43.75 | — |
| Chlorohydrate (3) | — | 32.0 |
| De-mineralised water | — | 11.75 |
| Perfume | 1.0 | 1.0 |

(1) Hyroxypropyl cellulose
(2) 37% zirconium aluminium chlorohydrate
(3) 50% aluminium chlorohydrate Thereafter the degree of sweating is monitored by video microscopy. Measurement of active glands was performed using a Mitsubishi Microwatcher deep field microscope equipped with a zoom lens (40–200×magnification), linked to a Sony television monitor and a Panasonic AG-6124 VHS video cassette recorder. Recordings were made of areas of skin onto which a layer of mineral oil (Sigma) had been applied.

The oil was held in place by a specially designed brass cup attached to the microscope which also served to keep the distance between the lens and the skin surface constant during use. Sweat emerging from individual glands appears as spherical droplets in the oil layer. To visualise the droplets it was necessary to enhance their contrast by introducing angled light to the surface of the skin from a fibre optic light source, rather than use the vertical light produced by the intrinsic light source of the Microwatcher. Angled light was produced from a Schott fibre optic light source.

To measure numbers of active glands per unit area of skin video recordings were made of relatively large areas of skin (approximately 50 mm$^2$) and the number of sweat droplets generated over a measured period of time (approximately 3 minutes) was then counted. The video sequences were calibrated using a 15 mm calibration disc immediately proceeding or following each recording.

Results

| | | | Glands/mm$^2$ post Treatment | | | | | |
|---|---|---|---|---|---|---|---|---|
| | pH | | Without Iontophoresis/ACTZ | | | With Iontophoesis/ACTZ | | |
| Subject | Untreated | Treated | Control | B | A | Control | B | A |
| Mean | 4.598 | 4.778 | 0.557 | 0.519 | 0.523 | 0.600 | 0.456 | 0.370 |
| St.Error include .SubjVar | 0.074 | 0.110 | 0.048 | 0.071 | 0.064 | 0.071 | 0.061 | 0.063 |
| St. Error excl. SubjVar | 0.046 | 0.046 | 0.056 | 0.056 | 0.056 | 0.056 | 0.056 | 0.056 |
| Statistical Significant | P < 0.004 | | ns | | | P < 0.01 | | |

ACTZ = acetazolamide (Diamox ™ powder)

On the treated areas where no iontophoresis/acetazolamide pretreatment was carried out, it was found that there was no significant difference in the sweating observed between the control test area and the areas treated with compositions A and B.

However, on the test sites where iontophoresis/acetazolamide pretreatment had been carried out, there was a significant decrease in the amount of sweating observed between the control site and the site treated with composition B, and a further significant decrease in sweating between the area treated with composition B (ie the relatively low efficacy composition) compared to the area treated with composition A (ie the relatively high efficacy composition). The efficacy of compositions A and B as applied to acetazolamide pretreated sites was also significantly higher compared to the corresponding applications of compositions A and B on sites which were not acetazolamide pretreated.

More specifically, when the protocol for application using this technique was performed in the presence of aluminium containing formulations (n=9), a significant decrease in the number of active glands was shown (P<0.01) for the high efficacy antiperspirant (A). This was accompanied by a statistically significant elevation of sweat pH (P<0.004) which supports the original hypothesis that an induced increase in eccrine sweat pH can consequently improve aluminium antiperspirant efficacy.

It is thought that the increase in efficacy observed can be attributed to the increase in sweat pH caused by the application of acetazolamide.

EXAMPLE 3

In Vitro Testing

A segment of reabsorptive duct was dissected from an isolated sweat gland, set up between glass pipettes and superfused with bicarbonate buffered physiological saline on the stage of an Olympus IMT-2 inverted microscope connected to a Photon Technology International Deltascan dual excitation fluorescence system.

In order to determine the activity of carbonic anhydrase in vitro and hence the ability of the duct to reabsorb bicarbonate, $HCO_3^-$ and $CO_2$ were simultaneously removed from the external bathing medium and the effects upon intracellular pH measured using the fluorescent dye BCECF. This manoeuvre results in an initial alkalinisation of intracellular pH ($\Delta pH_{alk}$) due to the rapid exit of $CO_2$ followed by a recovery of pH ($\Delta pH_{rec}$) due to the slower exit of $HCO_3^-$. As the interconversion between $HCO_3^-$ and $CO_2$ within the cell depends upon the presence of carbonic anhydrase, the magnitude of $\Delta pH_{alk}$ provides an indication of the activity of this enzyme in vitro.

Results

In a first series of experiments, under control conditions, the value of $\Delta pH_{alk}$ was 0.22±0.09 pH units. Administration of acetazolamide, a known inhibitor of carbonic anhydrase, significantly reduced $\Delta pH_{alk}$ by 68.18% to a value of 0.07±0.03 (n=5, P<0.01).

Table 1 shows the effects of the administration of Sibercizer C6 (N-ethyl-O and P-toluenesulfonamide) on the pH changes associated with the removal of $HCO_3^-$ and $CO_2$ from the bathing medium in the isolated unperfused eccrine sweat duct. From these results, it can be seen that administration of Sibercizer C6 in vitro produces a dose dependent inhibition of $\Delta pH_{alk}$, indicative of an inhibition of carbonic anhydrase activity.

TABLE 1

|  | 5.98 mMSC6 (n = 5) | 1 mM SC6 (n = 7) | 0.1 mM SC6 (n = 4) | 0.01 mM SC6 (n = 2) |
|---|---|---|---|---|
| $\Delta pH_{alk}$ Before SC6 | 0.334 ± 0.02 | 0.261 ± 0.02 | 0.269 ± 0.02 | 0.139 ± 0.02 |
| $\Delta pH_{alk}$ After SC6 | 0.102 ± 0.02 | 0.127 ± 0.01 | 0.145 ± 0.02 | 0.113 ± 0.00 |
| % reduction from control | 69.46* | 51.34* | 46.09* | 18.71* | note: 1) SC6 - Sibercizer C6
2) *denotes a significant decrease from control value (P < 0.01)

EXAMPLE 4

Further in Vitro Testing

In a further series of experiments, performed as in Example 3, 0.02% Dorzolamide hydrochloride (Trusopt™, ex Merck, Sharpe and Dohme) also led to a reduction of $\Delta pH_{alk}$ by 50.31% from 0.126±0.02 pH units under control conditions to 0.062±0.01 pH units with Dorzolamide (n=9, P<0.05).

What is claimed is:

1. An antiperspirant product for application to the human skin, comprising an antiperspirant active for topical application, and an effective amount of a compound which inhibits the acidification mechanism in the eccrine gland to elevate the pH of sweat.

2. A product according to claim 1, wherein the compound which elevates the pH of sweat is a bicarbonate reabsorption inhibitor.

3. A product according to claim 2, wherein the bicarbonate reabsorption inhibitor is a carbonic anhydrase inhibitor.

4. A product according to claim 3, wherein the carbonic anhydrase inhibitor is a sulphonamide.

5. A product according to claim 1, wherein the compound which elevates the pH of sweat in the eccrine gland is acetazolamide, ethyl tosylamide, dorzolamide or sezolamide.

6. A product according to claim 1, wherein the antiperspirant active material is one of aluminium chlorohydrate, activated aluminium chlorohydrate, zirconium aluminium chlorohydrate, zirconium aluminium glycinate, and activated zirconium aluminium glycinate.

7. A product according to claim 1, wherein the antiperspirant active is in the form of a solution, suspension, emulsion or microemulsion.

8. A product according to claim 1, wherein the antiperspirant active is in the form of an aerosol, pump spray, stick, soft solid, cream, gel or roll on lotion.

9. A cosmetic method of elevating the pH of sweat in the eccrine gland comprising topically applying thereto an effective amount of a compound which raises the pH of sweat in the gland.

10. A cosmetic method of preventing perspiration of the human body, comprising topically applying to the body a composition comprising an antiperspirant active, and also applying a compound which elevates the pH of sweat in the eccrine gland.

11. An antiperspirant composition for topical application to the human skin, comprising an antiperspirant active, and an effective amount of a compound which elevates the pH of sweat in the eccrine gland.

12. A cosmetic method of preventing perspiration of the human body, comprising topically applying to the body a composition comprising an antiperspirant active and a compound which elevates the pH of sweat in the eccrine gland.

13. An antiperspirant or deodorant composition for topical application to the human skin, comprising an antiperspirant or deodorant active and an effective amount of a carbonic anhydrase inhibitor selected from the group consisting of acetazolamide, sibercizer C6, dorzolamide, sezolamide and ethyl tosylamide.

* * * * *